(12) United States Patent
Hanenburg (10) Patent No.: US 12,156,979 B2
(45) Date of Patent: Dec. 3, 2024

(54) DEFLECTABLE CATHETER SHAFT WITH PULLWIRE ANCHOR FEATURE

(71) Applicant: St. Jude Medical, Cardiology Division, Inc., St. Paul, MN (US)

(72) Inventor: Amy L. Hanenburg, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 232 days.

(21) Appl. No.: 16/418,176

(22) Filed: May 21, 2019

(65) Prior Publication Data

US 2019/0351189 A1 Nov. 21, 2019

Related U.S. Application Data

(60) Provisional application No. 62/674,330, filed on May 21, 2018.

(51) Int. Cl.
*A61M 25/01* (2006.01)
*A61M 25/00* (2006.01)
(Continued)

(52) U.S. Cl.
CPC .... *A61M 25/0147* (2013.01); *A61M 25/0012* (2013.01); *A61M 25/0045* (2013.01);
(Continued)

(58) Field of Classification Search
CPC .......... A61M 25/0147; A61M 25/0045; A61M 25/0012; A61M 2025/015; A61M 25/005;
(Continued)

(56) References Cited

U.S. PATENT DOCUMENTS 4,799,474 A * 1/1989 Ueda ............... A61M 25/09033
604/291
4,920,980 A * 5/1990 Jackowski ........... A61N 1/0565
604/95.04
(Continued)

FOREIGN PATENT DOCUMENTS

| CN | 101927053 B | 1/2015 |
| CN | 103157168 B | 4/2015 |

(Continued)

OTHER PUBLICATIONS

"Adjacent.", 2011, Houghton Mifflin Harcourt Publishing Company, American Heritage® Dictionary of the English Language, Fifth Edition. (Year: 2011).*

(Continued)

*Primary Examiner* — William R Carpenter
*Assistant Examiner* — Robert F Allen
(74) *Attorney, Agent, or Firm* — Kilpatrick Townsend & Stockton LLP (57) ABSTRACT

Various embodiments of the present disclosure can include a deflectable catheter shaft. The deflectable catheter shaft can include a tubular elongated body including a wall, an inner surface of which circumferentially surrounds and defines a central lumen extending a length of the tubular elongated body, the tubular elongated body extending along a longitudinal axis and comprising a body distal end and a body proximal end. The deflectable catheter shaft can include a pullwire, wherein the pullwire includes a pullwire proximal end and a pullwire distal end, and wherein the pullwire extends along the tubular elongated body. The deflectable catheter shaft can include an anchor feature coupled to the pullwire distal end, wherein the anchor feature is embedded in the wall of the body distal end.

13 Claims, 7 Drawing Sheets

(51) Int. Cl.
*A61B 1/005* (2006.01)
*A61B 17/00* (2006.01)

(52) U.S. Cl.
CPC ....... *A61B 1/0057* (2013.01); *A61B 2017/003* (2013.01); *A61M 25/0133* (2013.01); *A61M 25/0136* (2013.01); *A61M 2025/015* (2013.01); *A61M 2025/0161* (2013.01)

(58) Field of Classification Search
CPC ....... A61M 25/014; A61B 2017/22038; A61B 2017/22045; A61B 2017/22042
See application file for complete search history.

(56) References Cited

U.S. PATENT DOCUMENTS

| | | | |
|---|---|---|---|
| 5,224,939 | A | 7/1993 | Holman et al. |
| 5,318,525 | A * | 6/1994 | West ................. A61B 18/1492 |
| | | | 604/95.04 |
| 5,380,301 | A | 1/1995 | Prichard et al. |
| 5,381,782 | A * | 1/1995 | DeLaRama .......... A61B 1/0056 |
| | | | 604/95.01 |
| 5,397,304 | A * | 3/1995 | Truckai ............ A61M 25/0147 |
| | | | 604/528 |
| 5,400,783 | A | 3/1995 | Pomeranz et al. |
| 5,456,254 | A | 10/1995 | Pietroski et al. |
| 5,626,136 | A | 5/1997 | Webster, Jr. |
| 5,676,653 | A * | 10/1997 | Taylor ............... A61M 25/0144 |
| | | | 604/95.04 |
| 5,715,817 | A | 2/1998 | Stevens-Wright et al. |
| 5,715,832 | A | 2/1998 | Koblish et al. |
| 5,827,278 | A | 10/1998 | Webster, Jr. |
| 5,876,373 | A | 3/1999 | Giba et al. |
| 6,074,379 | A | 6/2000 | Prichard |
| 6,146,355 | A * | 11/2000 | Biggs ................. A61M 25/0147 |
| | | | 604/95.04 |
| 6,273,404 | B1 | 8/2001 | Holman et al. |
| 6,491,681 | B1 | 12/2002 | Kunis et al. |
| 6,554,794 | B1 | 4/2003 | Mueller et al. |
| 7,004,937 | B2 | 2/2006 | Lentz et al. |
| 7,056,314 | B1 * | 6/2006 | Florio ................. A61M 25/0147 |
| | | | 604/95.01 |
| 7,214,220 | B2 | 5/2007 | McGlinch et al. |
| 7,217,256 | B2 | 5/2007 | Di Palma |
| 7,608,063 | B2 | 10/2009 | Le et al. |
| 7,625,365 | B2 | 12/2009 | McGlinch et al. |
| 7,666,204 | B2 | 2/2010 | Thornton et al. |
| 7,959,601 | B2 | 6/2011 | McDaniel et al. |
| 7,985,215 | B2 | 7/2011 | Guo et al. |
| 8,103,327 | B2 | 1/2012 | Harlev et al. |
| 8,137,321 | B2 | 3/2012 | Argentine |
| 8,187,267 | B2 | 5/2012 | Pappone et al. |
| 8,221,390 | B2 | 7/2012 | Pal et al. |
| 8,273,016 | B2 | 9/2012 | O'Sullivan |
| 8,376,990 | B2 | 2/2013 | Ponzi et al. |
| 8,447,377 | B2 | 5/2013 | Harlev et al. |
| 8,608,703 | B2 | 12/2013 | Riles et al. |
| 8,649,880 | B1 | 2/2014 | Parker, Jr. |
| 8,700,120 | B2 | 4/2014 | Koblish |
| 8,706,193 | B2 | 4/2014 | Govari et al. |
| 8,755,861 | B2 | 6/2014 | Harlev et al. |
| 8,777,929 | B2 | 7/2014 | Schneider et al. |
| 8,792,962 | B2 | 7/2014 | Esguerra et al. |
| 8,814,824 | B2 | 8/2014 | Kauphusman et al. |
| 8,814,825 | B2 | 8/2014 | Tegg et al. |
| 8,882,705 | B2 | 11/2014 | McDaniel et al. |
| 8,894,610 | B2 | 11/2014 | Macnamara et al. |
| 8,996,091 | B2 | 3/2015 | de la Rama et al. |
| 9,017,308 | B2 | 4/2015 | Klisch et al. |
| 9,033,917 | B2 | 5/2015 | Magana et al. |
| 9,050,010 | B2 | 6/2015 | Bui et al. |
| 9,101,733 | B2 | 8/2015 | McDaniel |
| 9,204,929 | B2 | 12/2015 | Solis |
| 9,216,056 | B2 | 12/2015 | Datta et al. |
| 9,247,990 | B2 | 2/2016 | Kauphusman et al. |
| 9,326,815 | B2 | 5/2016 | Watson |
| 9,339,631 | B2 | 5/2016 | Graham et al. |
| 9,433,751 | B2 | 9/2016 | Ponzi et al. |
| 9,433,752 | B2 | 9/2016 | Jimenez et al. |
| 9,468,495 | B2 | 10/2016 | Kunis et al. |
| 9,486,280 | B2 | 11/2016 | Koblish et al. |
| 9,486,282 | B2 | 11/2016 | Solis |
| 9,539,413 | B2 | 1/2017 | Ogle |
| 9,649,158 | B2 | 5/2017 | Datta et al. |
| 9,687,166 | B2 | 6/2017 | Subramaniam et al. |
| 9,693,733 | B2 | 7/2017 | Altmann et al. |
| 9,694,159 | B2 | 7/2017 | Schneider et al. |
| 9,694,161 | B2 | 7/2017 | Selkee |
| 9,788,895 | B2 | 10/2017 | Solis |
| 9,820,664 | B2 | 11/2017 | Hoitink et al. |
| 9,844,645 | B2 | 12/2017 | Pai et al. |
| 9,848,795 | B2 | 12/2017 | Marecki et al. |
| 9,855,404 | B2 * | 1/2018 | Romoscanu ...... A61M 25/0147 |
| 9,919,132 | B2 | 3/2018 | Tegg et al. |
| 9,949,656 | B2 | 4/2018 | Wu et al. |
| 9,986,949 | B2 | 6/2018 | Govari et al. |
| 10,004,877 | B2 | 6/2018 | Tegg |
| 10,034,637 | B2 | 7/2018 | Harlev et al. |
| 10,052,457 | B2 | 8/2018 | Nguyen et al. |
| 10,065,019 | B2 | 9/2018 | Hamuro et al. |
| 10,099,036 | B2 | 10/2018 | Heideman et al. |
| 10,118,022 | B2 | 11/2018 | Helgeson et al. |
| 10,143,394 | B2 | 12/2018 | Solis |
| 10,322,261 | B2 | 6/2019 | Pai et al. |
| 10,362,952 | B2 | 7/2019 | Basu et al. |
| 10,362,954 | B2 | 7/2019 | de la Rama et al. |
| 10,376,170 | B2 | 8/2019 | Quinn et al. |
| 10,384,036 | B2 | 8/2019 | Romoscanu |
| 10,398,500 | B2 | 9/2019 | Huszar et al. |
| 10,478,325 | B2 | 11/2019 | Syed |
| 10,506,938 | B2 | 12/2019 | Wu et al. |
| 10,537,259 | B2 | 1/2020 | Wu et al. |
| 10,542,899 | B2 | 1/2020 | Wu et al. |
| 10,556,091 | B2 | 2/2020 | Truhler et al. |
| 10,575,742 | B2 | 3/2020 | Wu et al. |
| 10,575,745 | B2 | 3/2020 | Solis |
| 10,595,738 | B2 | 3/2020 | Sterrett et al. |
| 10,595,740 | B2 | 3/2020 | Hoitink et al. |
| 10,602,948 | B2 | 3/2020 | Wu et al. |
| 10,646,692 | B2 | 5/2020 | Tegg et al. |
| 10,653,423 | B2 | 5/2020 | Starnes |
| 10,702,677 | B2 | 7/2020 | Okamura et al. |
| 10,737,060 | B2 | 8/2020 | Gupta et al. |
| 10,835,712 | B2 | 11/2020 | Wada |
| 10,842,990 | B2 | 11/2020 | de la Rama et al. |
| 10,857,349 | B2 | 12/2020 | de la Rama et al. |
| 10,869,992 | B2 | 12/2020 | Pai et al. |
| 10,898,685 | B2 | 1/2021 | Tegg |
| 10,912,925 | B2 | 2/2021 | Houck |
| 10,945,626 | B2 | 3/2021 | Fuentes-Ortega et al. |
| 10,953,196 | B2 | 3/2021 | Raab et al. |
| 10,959,636 | B2 | 3/2021 | Dahlen et al. |
| 10,966,623 | B2 | 4/2021 | Wu et al. |
| 10,966,753 | B2 | 4/2021 | Coyle et al. |
| 10,967,150 | B2 | 4/2021 | Helgeson et al. |
| 10,987,045 | B2 | 4/2021 | Basu et al. |
| 11,033,715 | B2 | 6/2021 | Beeckler et al. |
| 11,039,772 | B2 | 6/2021 | Wu et al. |
| 11,039,773 | B2 | 6/2021 | Sterrett et al. |
| 11,083,400 | B2 | 8/2021 | Hoitink et al. |
| 11,116,436 | B2 | 9/2021 | Wu et al. |
| 11,116,476 | B2 | 9/2021 | Buesseler et al. |
| 11,123,051 | B2 | 9/2021 | Van Der Linde et al. |
| 11,141,568 | B2 | 10/2021 | Hsueh et al. |
| 11,160,482 | B2 | 11/2021 | Solis |
| 11,172,858 | B2 | 11/2021 | Olson et al. |
| 11,272,886 | B2 | 3/2022 | Harlev et al. |
| 2001/0025134 | A1 * | 9/2001 | Bon .................. A61M 25/0144 |
| | | | 600/146 |
| 2002/0165484 | A1 | 11/2002 | Bowe et al. |
| 2004/0122360 | A1 * | 6/2004 | Waldhauser ........ A61M 25/005 |
| | | | 264/234 |
| 2006/0074383 | A1 * | 4/2006 | Boulais ............... A61B 1/0057 |
| | | | 604/95.04 |

(56) References Cited

U.S. PATENT DOCUMENTS

| | | | |
|---|---|---|---|
| 2007/0005008 A1* | 1/2007 | Honebrink | A61M 25/0147 604/95.04 |
| 2007/0178131 A1* | 8/2007 | Yamada | A61M 25/0009 604/500 |
| 2007/0270679 A1* | 11/2007 | Nguyen | A61M 25/0043 600/585 |
| 2008/0188800 A1* | 8/2008 | Bencini | A61M 25/0141 604/95.04 |
| 2010/0152731 A1 | 6/2010 | de la Rama et al. | |
| 2010/0168666 A1* | 7/2010 | Tegg | A61M 25/0147 604/95.04 |
| 2010/0317962 A1* | 12/2010 | Jenkins | A61B 18/18 600/411 |
| 2012/0089125 A1* | 4/2012 | Scheibe | A61M 25/0147 604/523 |
| 2013/0281925 A1* | 10/2013 | Benscoter | A61B 1/0125 604/95.04 |
| 2014/0100639 A1 | 4/2014 | Lee et al. | |
| 2014/0330251 A1* | 11/2014 | Romoscanu | A61M 25/0147 604/95.04 |
| 2015/0119911 A1 | 4/2015 | Mckenzie | |
| 2015/0283356 A1* | 10/2015 | Kanemasa | A61M 25/0012 29/418 |
| 2016/0158497 A1* | 6/2016 | Tran | A61F 2/2436 623/2.11 |
| 2016/0213423 A1 | 7/2016 | Kauphusman et al. | |
| 2016/0278851 A1* | 9/2016 | Mannion | A61M 25/0045 |
| 2016/0331933 A1 | 11/2016 | Knutsen | |
| 2017/0106170 A1* | 4/2017 | Hsueh | A61M 25/0147 |
| 2017/0258614 A1* | 9/2017 | Griffin | A61F 2/966 |
| 2017/0319269 A1 | 11/2017 | Oliverius et al. | |
| 2017/0367756 A1 | 12/2017 | Sliwa et al. | |
| 2018/0042667 A1 | 2/2018 | Pappone et al. | |
| 2018/0085064 A1 | 3/2018 | Auerbach et al. | |
| 2018/0161093 A1 | 6/2018 | Basu et al. | |
| 2018/0229030 A1 | 8/2018 | Dubuclet et al. | |
| 2018/0296801 A1* | 10/2018 | Tegg | A61M 25/0012 |
| 2018/0369574 A1 | 12/2018 | Dubuclet et al. | |
| 2019/0009052 A1 | 1/2019 | Oliverius et al. | |
| 2019/0117937 A1* | 4/2019 | Humphrey | A61M 25/0147 |
| 2019/0125378 A1 | 5/2019 | Shelton, IV et al. | |
| 2019/0192826 A1 | 6/2019 | Wada | |
| 2020/0121894 A1 | 4/2020 | Prabhu et al. | |
| 2020/0138378 A1 | 5/2020 | de la Rama et al. | |
| 2020/0214635 A1 | 7/2020 | Dahlen et al. | |
| 2020/0253496 A1 | 8/2020 | Deno et al. | |
| 2020/0405166 A1 | 12/2020 | Wu et al. | |
| 2021/0145342 A1 | 5/2021 | Wang | |
| 2021/0153932 A1 | 5/2021 | Voth et al. | |
| 2021/0187246 A1 | 6/2021 | Houck | |
| 2021/0204871 A1 | 7/2021 | Goedeke et al. | |
| 2021/0268234 A1 | 9/2021 | Helgeson et al. | |
| 2021/0298656 A1 | 9/2021 | Wu et al. | |
| 2021/0361216 A1 | 11/2021 | Hoitink et al. | |
| 2021/0401345 A1 | 12/2021 | Wu et al. | |
| 2022/0023594 A1 | 1/2022 | Pai | |
| 2022/0054066 A1 | 2/2022 | Solis | |
| 2022/0061727 A1 | 3/2022 | Olson et al. | |

FOREIGN PATENT DOCUMENTS

| | | |
|---|---|---|
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 110536646 A | 12/2019 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2604306 B1 | 1/2014 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3531903 A1 | 9/2019 |
| EP | 3434218 B1 | 3/2020 |
| EP | 2908723 B1 | 3/2020 |
| EP | 3114987 B1 | 8/2020 |
| EP | 3178516 B1 | 9/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3749195 A1 | 12/2020 |
| EP | 3750475 A1 | 12/2020 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3932343 A4 | 1/2022 |
| EP | 3791820 B9 | 4/2022 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |

(56) References Cited

FOREIGN PATENT DOCUMENTS

| | | | |
|---|---|---|---|
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 5/2019 |
| JP | 6528010 B1 | 6/2019 |
| JP | 6655655 B2 | 2/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 2021523755 A | 9/2021 |
| JP | 6980386 B2 | 11/2021 |
| JP | 2022020838 A | 2/2022 |
| WO | 9843530 A1 | 10/1998 |
| WO | 0168178 A1 | 9/2001 |
| WO | 2008091197 A1 | 7/2008 |
| WO | 2017098198 A1 | 6/2017 |
| WO | 2018053148 A1 | 3/2018 |
| WO | 2018053164 A1 | 3/2018 |
| WO | 2018136741 A1 | 7/2018 |
| WO | 2019195439 A1 | 10/2019 |

OTHER PUBLICATIONS

"Assembly.", 2014, HarperCollins Publishers, Collins English Dictionary—Complete and Unabridged, 12th Edition. (Year: 2014).*

* cited by examiner

DEFLECTABLE CATHETER SHAFT WITH PULLWIRE ANCHOR FEATURE

CROSS-REFERENCE TO RELATED APPLICATIONS

This application claims the benefit of U.S. provisional application No. 62/674,330, filed 21 May 2018, which is hereby incorporated by reference as though fully set forth herein.

BACKGROUND a. Field

The instant disclosure relates to a deflectable catheter shaft with pullwire anchor feature.

b. Background Art

Electrophysiology catheters can be used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

Typically, a catheter can be deployed and manipulated through a patient's vasculature to the intended site, for example, a site within a patient's heart or a chamber or vein thereof. To position a catheter within the body at a desired site, some type of navigation may be used, such as mechanical steering features incorporated into the catheter (or an introducer sheath). In some examples, medical personnel can manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pullwire attached at the distal end of the catheter that extends to a control handle that controls the application of tension on the pullwire.

The foregoing discussion is intended only to illustrate the present field and should not be taken as a disavowal of claim scope.

BRIEF SUMMARY

Various embodiments of the present disclosure can include a deflectable catheter shaft. The deflectable catheter shaft can include a tubular elongated body including a wall, an inner surface of which circumferentially surrounds and defines a central lumen extending a length of the tubular elongated body, the tubular elongated body extending along a longitudinal axis and comprising a body distal end and a body proximal end. The deflectable catheter shaft can include a pullwire, wherein the pullwire includes a pullwire proximal end and a pullwire distal end, and wherein the pullwire extends along the tubular elongated body. The deflectable catheter shaft can include an anchor feature coupled to the pullwire distal end, wherein the anchor feature is embedded in the wall of the body distal end.

Various embodiments of the present disclosure include a deflectable catheter shaft. The deflectable catheter shaft can include a tubular elongated body including a wall, an inner surface of which circumferentially surrounds and defines a central lumen extending therethrough, the tubular elongated body extending along a longitudinal axis and comprising a body distal end and a body proximal end. The deflectable catheter shaft can include a tubular anchor segment connected to the body distal end. The deflectable catheter shaft can include a first pullwire and a second pullwire, wherein each of the first and second pullwires include a pullwire proximal end and a pullwire distal end, and wherein the first and second pullwires extend along the tubular elongated body. The deflectable catheter shaft can include a first anchor feature coupled to the first pullwire distal end and a second anchor feature coupled to the second pullwire distal end, wherein the first and second anchor features are embedded in the tubular anchor segment.

Various embodiments of the present disclosure can include a method for forming a deflectable catheter shaft. The method can include embedding an anchor feature disposed on a distal end of a pullwire into a polymer anchor segment. The method can include inserting the pullwire into a lumen of a pullwire liner to form a pullwire assembly. The method can include positioning the pullwire assembly on a mandrel. The method can include positioning a braid layer over the mandrel and the pullwire liner. The method can include positioning a polymer elongated body over the pullwire assembly and the braid layer such that a distal end of the elongated body is in contact with a proximal end of the polymer anchor segment to form a preassembly. The method can include reflowing the preassembly to form the deflectable catheter shaft.

The foregoing and other aspects, features, details, utilities, and advantages of the present invention will be apparent from reading the following description and claims, and from reviewing the accompanying drawings.

DETAILED DESCRIPTION

Figure 1:
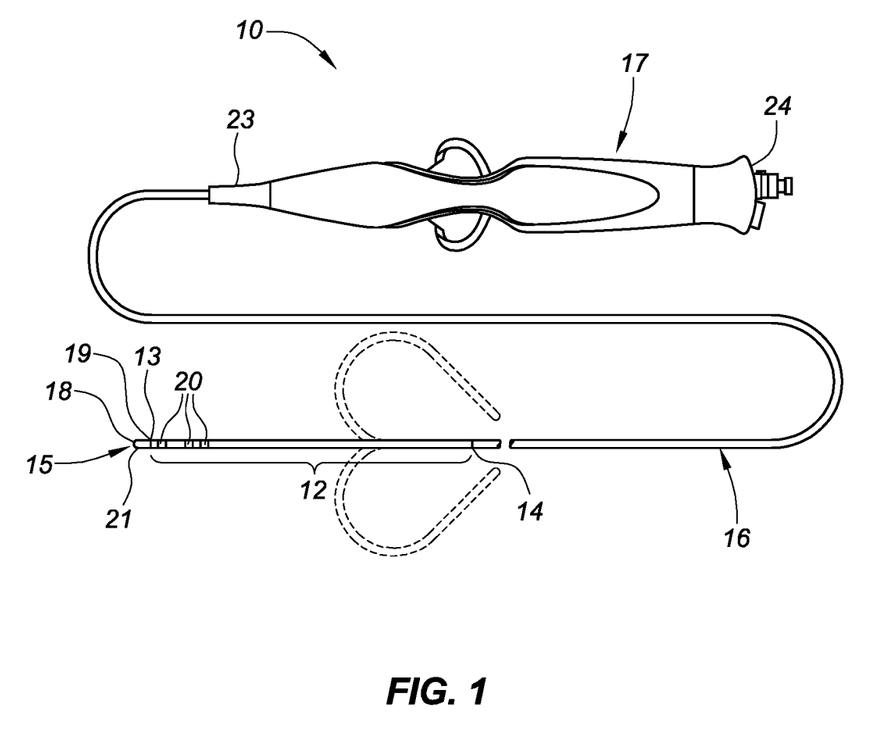
FIG. 1 illustrates a deflectable electrophysiology catheter that comprises a deflectable catheter shaft section, in accordance with embodiments of the present disclosure.

FIG. 1 illustrates a deflectable electrophysiology catheter that comprises a deflectable catheter shaft section in accordance with embodiments of the present disclosure. Deflectable catheter shaft section 12 includes a tubular elongated body having a distal end 13 and a proximal end 14. In its most general form, catheter 10 further includes a tip assembly 15 located at the distal end 13 of the deflectable catheter shaft section 12, a proximal catheter shaft section 16 located at the proximal end 14 of the deflectable catheter shaft section 12, and a handle assembly 17. Catheter 10 can be used in any number of diagnostic and/or therapeutic applications, such as the recording of electrograms in the heart, the performance of a cardiac ablation procedure, and other similar applications/procedures. Accordingly, one of ordinary skill in the art will recognize and appreciate that the deflectable catheter shaft section and method of manufacturing the same can be used in any number of diagnostic and therapeutic applications.

The tip assembly 15 can comprise a tip electrode 21 having a distal end 18 and a proximal end 19. Tip electrode 21 can be configured for various functions and can include, without limitation, an active outer surface that is configured for exposure to blood and/or tissue. The tip electrode 21 can be affixed to distal end 13 of the deflectable catheter shaft section 12 in a number of ways. For instance, the tip electrode 21 can be bonded to an inner radial surface of the deflectable catheter shaft section 12 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 21 of the tip assembly 15 can have a recess formed therein that is sufficiently sized and configured to receive a wire that is connected to the tip electrode 21, as discussed herein. One end of the wire can be connected to the tip electrode 21 and the other end can be connected to, for example, monitoring or recording or ablation devices, such as a radiofrequency (RF) generator. The wire can be a pre-coated wire that is insulated from other components in the tip assembly 15. The tip electrode 21 of the tip assembly 15 can further include a lumen formed therein that is configured to receive a thermal sensor, as discussed herein. The thermal sensor can be configured to measure the temperature of the tip electrode 21, targeted tissue, and/or the interface therebetween and provide feedback to the monitoring or recording or ablation devices described hereinabove. The tip electrode 21 can further include a fluid lumen manifold configured as a passageway for irrigation fluid.

The proximal catheter shaft section 16 can also include one or more lumens. The proximal catheter shaft section 16 can be constructed of a series of polymer layer(s) and braid structure(s). In particular, one or more wires wound to form a cylindrical braid structure can substantially surround the one or more lumens of proximal catheter shaft section 16. In addition, a polymeric material, such as polyurethane, nylon, or various types of plastic materials such as polyether block amides offered under the trademark PEBAX®, or any other suitable material, can also substantially surround the one or more lumens of proximal catheter shaft section 16. The material can have the capability to be displaced and/or to shrink when subjected to a process, such as for example, a heating process that is performed. The mechanical properties of the proximal catheter shaft section 16 can also be varied by varying the properties of the cylindrical braid structure(s) and the polymeric material (e.g., dimension of the cylindrical braid structure and/or durometers of the polymers). Additionally, the mechanical properties of the proximal catheter shaft section 16, can be varied along the length of the proximal catheter shaft section 16. Alternatively, the mechanical properties of the proximal catheter shaft section 16 can be substantially constant along the entire length of the proximal catheter shaft section 16.

The deflectable catheter shaft section 12 can be disposed between the tip assembly 15 and the proximal catheter shaft section 16 and can include a plurality of ring electrodes 20. The length and diameter of the deflectable catheter shaft section 12 can vary according to the application. Generally, the length of the deflectable catheter shaft section 12 can range from about 2 inches (18.8 mm) to about 6 inches (119.4 mm) and the diameter of the deflectable catheter shaft section 12 can range from about 5 French to about 12 French. The diameter of the deflectable catheter shaft section 12 can be about 7 French in accordance with some embodiments. Although these particular dimensions are mentioned in particular, the dimensions of the deflectable catheter shaft section 12 can vary in accordance with various applications of the deflectable catheter shaft section 12.

The deflectable catheter shaft section 12 can be configured for deflection independent of the proximal catheter shaft section 16. The deflectable catheter shaft section 12 can be constructed of a series of polymer layer(s) and braid structure(s), which can be different than those used in the proximal catheter shaft section 16. In particular, one or more wires wound to form a cylindrical braid structure can substantially surround the one or more lumens of deflectable catheter shaft section 12. In addition, a polymeric material, such as polyurethane, nylon, or various types of plastic materials such as polyether block amides offered under the trademark PEBAX®, or any other suitable material, can also substantially surround the one or more lumens of deflectable catheter shaft section 12. The material can have the capability to be displaced and/or to shrink when subjected to a process, such as for example, a heating process that is performed. The mechanical properties of the deflectable catheter shaft section 12 can also be varied independent of the proximal catheter shaft section 16 by varying the properties of the cylindrical braid structure(s) and the polymeric material (e.g., dimension of the cylindrical braid structure and/or durometers of the polymers). Additionally, the mechanical properties of the deflectable catheter shaft section 12, can be varied along the length of the deflectable catheter shaft section 12. Alternatively, the mechanical properties of the deflectable catheter shaft section 12 can be substantially constant along the entire length of the deflectable catheter shaft section 12.

The handle assembly 17 can be coupled to the proximal catheter shaft section 16 at its proximal end (disposed within handle assembly 17 and not shown). The handle assembly 17 can be operative to, among other things, effect movement (i.e., deflection) of the deflectable catheter shaft section 12. The handle assembly 17 includes a distal end 23 and a proximal end 24. The handle assembly 17 includes an actuator that can be selectively manipulated to cause deflectable catheter shaft section 12 to deflect in one or more directions (e.g., up, down, left, and right). Deflectable catheter shaft section 12 can be configured for symmetric deflection in accordance with some embodiments and can be configured for asymmetric deflection in accordance with other embodiments, as discussed herein.

The catheter 10 can include any number of other elements such as, for example and without limitation, thermocouples, thermistor temperature sensors, etc. for monitoring the temperature of targeted tissue and controlling the temperature. In some embodiments, the catheter 10 can include a sensor for producing signals indicative of catheter location information, and can include one or more electrodes. In an example, the catheter 10 can include ring electrodes 20 that collectively define the sensor. The one or more electrodes can be provided on a distal end 13 of the catheter 10 and a localization system (e.g., EnSite™ Velocity™ system) can compute a distal location of the catheter 10 using received location information from the one or more electrodes and/or a geometrical relationship between the one or more electrodes. Although not depicted, the tip could include an ultrasound or other type of therapeutic or diagnostic sensor in addition to or in place of the tip electrode 21 and/or thermal sensor.

In various embodiments, the catheter 10 can include a flexible tip assembly, which can include, for example, a flexible tip electrode from a Therapy™ Cool Flex™ ablation catheter manufactured by St. Jude Medical, Inc. of St. Paul, Minnesota Additional details regarding a flexible electrode tip can be found in, for example, U.S. Pat. No. 8,187,267 B2 and United States patent application publication no. US 2010/0152731 A1, each of which is hereby incorporated by reference as though fully set forth herein.

Figure 2:
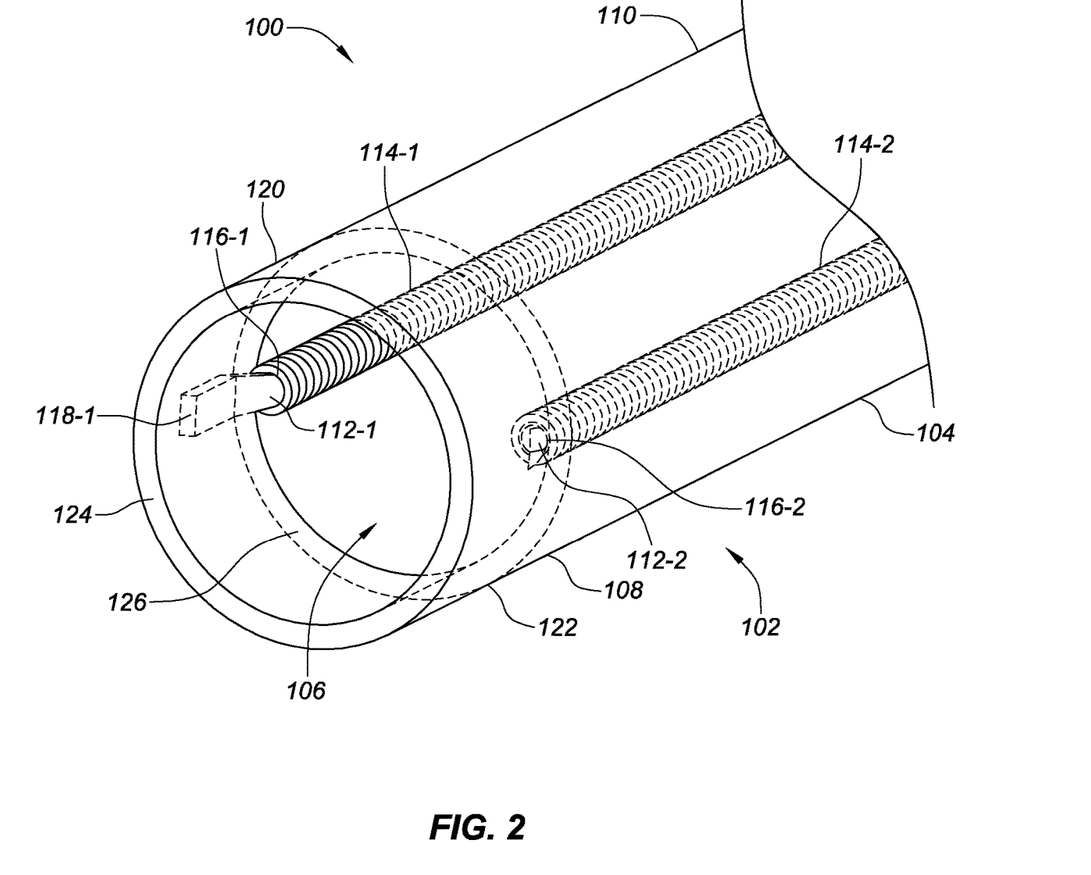
FIG. 2 illustrates a deflectable catheter shaft that includes an anchor feature, in accordance with embodiments of the present disclosure.

FIG. 2 illustrates a deflectable electrophysiology catheter 100 that comprises a deflectable catheter shaft 102, in accordance with embodiments of the present disclosure. In some embodiments, the deflectable catheter shaft 102 can include a tubular elongated body 104 that can be formed from a flexible material, such as a polymer material, for example. The tubular elongated body 104 can include a wall, the inner surface of which circumferentially surrounds and defines a central lumen 106 that extends therethrough. The central lumen 106 can provide a passageway for various components of the deflectable electrophysiology catheter 100 to pass. For example, a number of electrical components (e.g., wires), irrigation conduits, steering components (e.g., pullwires), etc. can pass through the central lumen 106. In some embodiments, the tubular elongated body 104 can include a body distal end 108 and a body proximal end 110.

In some embodiments, the tubular elongated body 104 can be deflected by one or more pullwires 112-1, 112-2 that extend through the wall of the tubular elongated body 104 and/or through the central lumen 106 of the tubular elongated body 104. The pullwires 112-1, 112-2 can include a pullwire proximal end and a pullwire distal end. In an example, the pullwires 112-1, 112-2 can be disposed inside of the wall of the tubular elongated body 104, in the central lumen 106 of the tubular elongated body 104, or partially within the central lumen 106 of the tubular elongated body 104 and in the wall of the tubular elongated body 104. Although two pullwires 112-1, 112-2 are depicted, which provides for a bidirectional deflectable electrophysiology catheter 100, fewer than or greater than two pullwires 112-1, 112-2 can be included in the tubular elongated body 104. For example, one pullwire can be included in the tubular elongated body 104, resulting in a unidirectional deflectable electrophysiology catheter 100; or more than two pullwires can be included in the tubular elongated body 104, resulting in an omnidirectional deflectable electrophysiology catheter 100. The pullwires 112-1, 112-2 can be disposed within pullwire liners 114-1, 114-2, together forming a pullwire assembly. The pullwire liners 114-1, 114-2 can define respective pullwire lumens 116-1, 116-2 through which the pullwires 112-1, 112-2 can extend.

As depicted in FIG. 2, the first pullwire 112-1 can include an anchor feature 118-1 that is coupled to a distal end of the first pullwire 112-1. Although not depicted, the second pullwire 112-2 can also include an anchor feature, which has not been depicted to better illustrate a cross-section of the second pullwire 112-2 and the second pullwire liner 114-2. In some embodiments, regardless of a number of pullwires included in the deflectable catheter shaft, some or all of the pullwires can include anchor features, such as anchor feature 118-1, coupled to their distal ends. Although anchor feature 118-1 is specifically discussed herein, the features discussed with respect to the anchor feature 118-1 can generally apply to some or all of the anchor features.

In some embodiments, the anchor feature 118-1 can be embedded in the wall of the body distal end 108. As depicted in FIG. 2, the body distal end 108 can include an anchor segment 120 into which the anchor feature 118-1 is embedded. The anchor segment 120 can be tubular and can be coaxial with a longitudinal axis defined by the tubular elongated body 104. In some embodiments, the anchor segment 120 can be formed from a material that has a durometer greater than that of adjacent portions of the tubular elongated body 104. For example, the anchor segment 120 can be attached to the body distal end 108 and can be formed from a material that has a durometer that is greater than that of the body distal end 108 and/or the tubular elongated body 104. In some embodiments, the anchor segment 120 can be formed from a material that has a durometer in a range from 63 to 72 Shore D. However, the durometer of the anchor segment 120 can be less than 63 Shore D or greater than 72 Shore D, in some embodiments. The tubular elongated body 104 can have a durometer from 35 to 45 Shore D. However, the durometer of the tubular elongated body 104 can be less than 35 Shore D or greater than 45 Shore D, in some embodiments.

In some embodiments, the anchor segment 120 can be formed from a polymer material, which can enable bonding of the anchor segment 120 to a polymer material that forms the tubular elongated body 104. For example, the anchor segment 120 can include a proximal segment end 122 and a distal segment end 124. The proximal segment end 122 can be coupled to the body distal end 108 at an interface 126, thus allowing for the central lumen to extend through the anchor segment 120. As depicted in FIG. 2, in some embodiments, an inner diameter of the anchor segment 120 can be the same as an inner diameter of the tubular elongated body 104. However, the inner diameter of the anchor segment 120 can be larger or smaller than the inner diameter of the tubular elongated body 104. As further depicted in FIG. 2, in some embodiments, an outer diameter of the anchor segment 120 can be the same as an outer diameter of the tubular elongated body 104. However, the outer diameter of the anchor segment 120 can be larger or smaller than the outer diameter of the tubular elongated body 104.

In some embodiments, the anchor feature 118-1 can be embedded in the wall of the anchor segment 120. For example, the anchor feature 118-1 can be molded within the anchor segment 120 via, for example, a reflow process. In some embodiments, the anchor segment 120 can be melt processed and during the melt processing of the anchor segment 120, the anchor feature 118-1 can be embedded in a sidewall of the anchor segment 118-1. In some embodiments, not depicted, the anchor segment 120 can be formed from an inner tubular segment and an outer tubular segment, both of which are formed from a polymer. The anchor feature 118-1 can be disposed between the inner tubular segment and the outer tubular segment and the inner tubular segment and the outer tubular segment can be reflowed, thus causing the anchor feature to be embedded between the inner tubular segment and the outer tubular segment. Embedding of the anchor feature 118-1 in the anchor segment 120 can result in the anchor feature 118-1 being immovable with respect to the anchor segment 120, allowing for tension applied to the first pullwire 112-1 to be transferred to the anchor segment 120 via the anchor feature 118-1. Through application of tension to one of the pullwires 112-1, 112-2, the deflectable electrophysiology catheter 100 can be deflected.

As previously mentioned, in some embodiments, the pullwire liners 114-1, 114-2 can provide pullwire lumens 116-1, 116-2 through which the pullwires 112-1, 112-2 can extend. In some embodiments, the pullwire liners 114-1, 114-2 can be polymer tubes. In an example, the pullwire liners 114-1, 114-2 can be micro-braided polyimide tubes. To promote adhesion between the pullwire liners 114-1, 114-2, the pullwire liners 114-1, 114-2 can include a thin film external layer made of a thermoplastic that can be configured to adhere to a polymer that forms the tubular elongated body 104. In some embodiments, the thin film external layer can be thermally adhered to the polymer that forms the tubular elongated body 104, however, the pullwire liners 114-1, 114-2 can be attached to the tubular elongated body 104 via other methods, as well, such as via an adhesive. The pullwire liners 114-1, 114-2 can include a lubricious lining that can enable free movement of the pullwires 112-1, 112-2 in the pullwire liners 114-1, 114-2. As tension is applied to the first pullwire 112-1, the pullwire 112-1 can be pulled through the respective first pullwire liner 114-1, thus pulling the anchor feature 118-1 proximally and exerting a force on the anchor segment 120, pulling the anchor segment 120 in the direction aligned with a longitudinal axis of the first pullwire 112-1.

As further discussed herein, the deflectable electrophysiology catheter 100 can include other components. For example, although not depicted, the deflectable electrophysiology catheter 100 can include a low friction liner disposed around an interior surface of the tubular elongated body 104. The low friction liner can extend from a proximal end of the tubular elongated body 104 to a distal end of the anchor segment 120. For instance, the low friction liner can be a tubular liner that is disposed about a mandrel on which the components of the deflectable electrophysiology catheter 100 are placed. Accordingly, the low friction liner can cover the inside wall of the tubular elongated body 104 as well as the portions of the pullwire liners 114-1, 114-2 that are exposed in the central lumen 106. Accordingly, the pullwire liners 114-1, 114-2 can be disposed between the low friction liner and the inside wall of the tubular elongated body 104. In some embodiments, the low friction liner can be formed from a low friction material, such as polytetrafluoroethylene.

In some embodiments, the low friction liner can be formed from, for example, a Teflon™ material.

Figure 6:
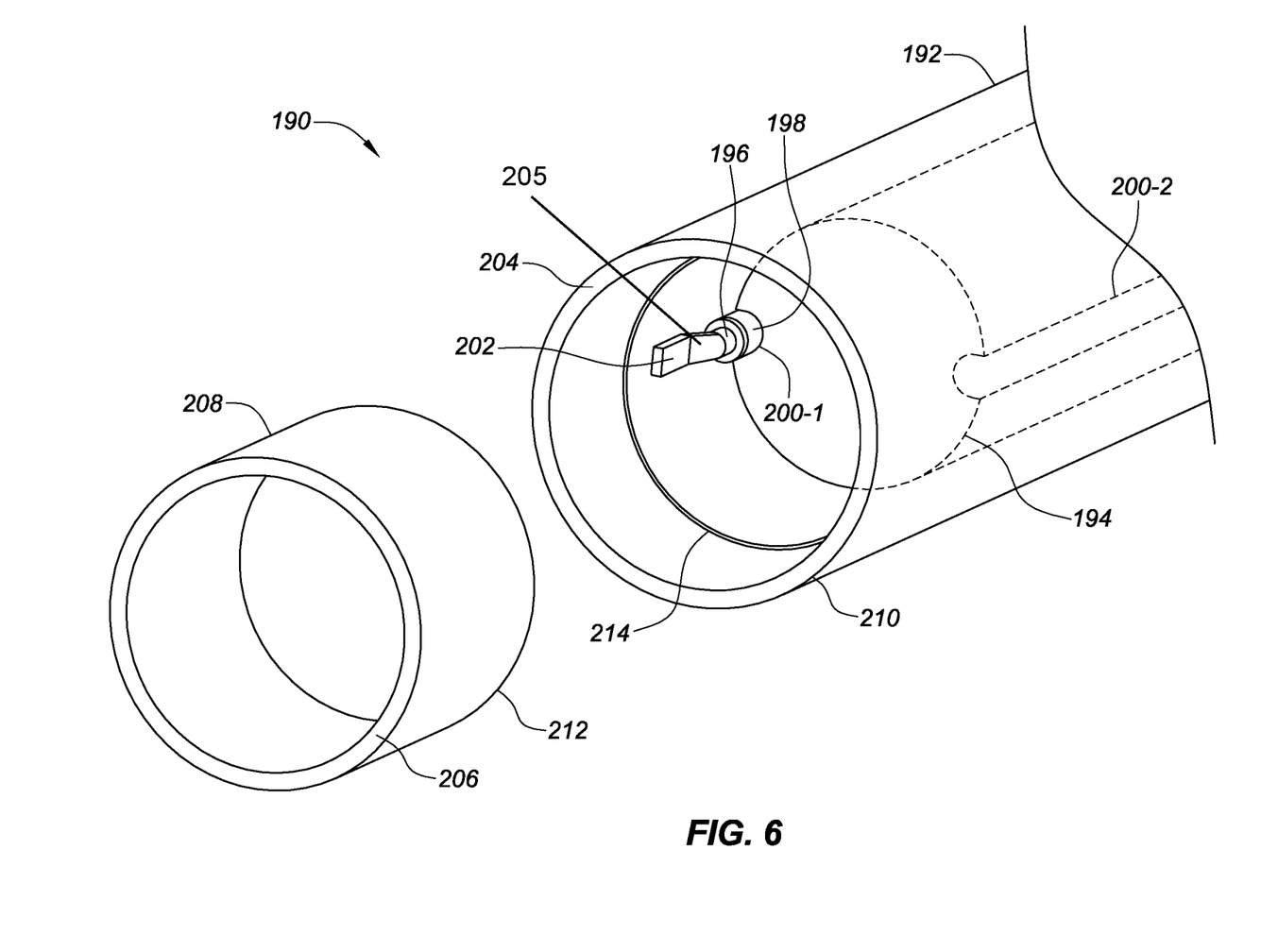
FIG. 6 illustrates a deflectable catheter shaft in a partially assembled state, in accordance with embodiments of the present disclosure.

In some embodiments, the deflectable electrophysiology catheter 100 can include a braid layer disposed between an inner surface of the tubular wall of the tubular elongated body 104 and the pullwire liners 114-1, 114-2, which is further depicted in FIG. 6. In some embodiments, the braid layer can be adhered to the inner surface of the wall of the tubular elongated body 104 and can further be adhered to the inner surface of the anchor segment 120. The braid layer can help maintain a shape of the tubular elongated body 104 when the tubular elongated body 104 is deflected. In some embodiments, as further discussed herein, the anchor feature 118-1 can be threaded through the braid layer, such that the anchor feature 118-1 is disposed within the wall of the anchor segment 120, while the braid layer is adhered to an inner surface of the anchor segment 120. In some embodiments, the pullwire liners 114-1, 114-2 can be adhered to an inner surface of the braid layer, which can in turn be adhered to the inner surface of the tubular elongated body 104, as previously discussed.

Figure 3A:
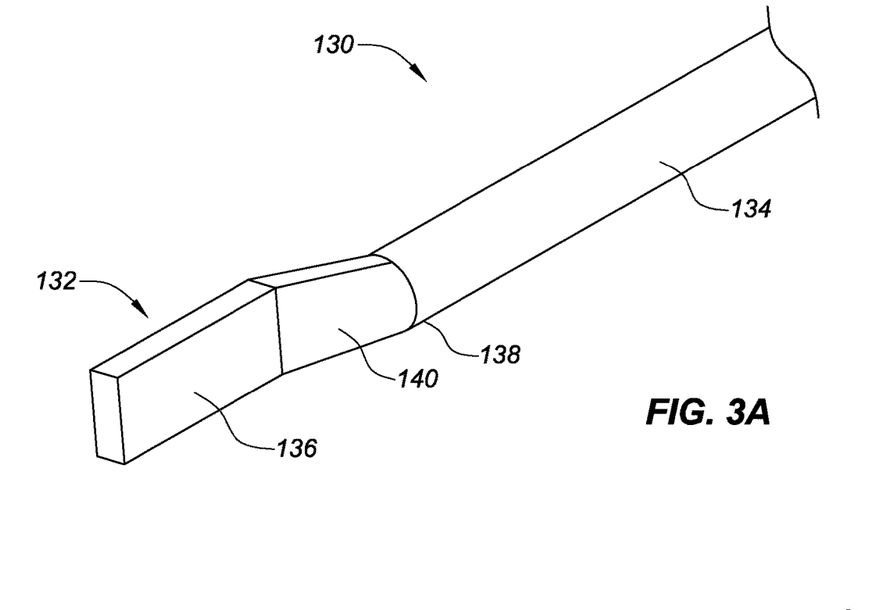
FIG. 3A illustrates a pullwire with a first type of anchor feature, in accordance with embodiments of the present disclosure.

FIG. 3A illustrates a pullwire 130 with a first type of anchor feature 132, in accordance with embodiments of the present disclosure. The pullwire 130 can include a pullwire shaft 134, which can be an elongated cylindrical structure in some embodiments. The pullwire shaft 134 can be formed from a metal, such as nitinol, or other suitable non-metallic materials. In some embodiments, the anchor feature can include a flattened end 136 (e.g., flattened portion), which is attached to a pullwire distal end 138 via an offset transition 140. Although the flattened end 136 is depicted as rectangular in shape, the flattened end 136 can be formed as other shapes in some embodiments. For example, in some embodiments, a distal end of the flattened end 136 can include flared features, which can extend perpendicular to a longitudinal axis of the pullwire 130.

Figure 3B:
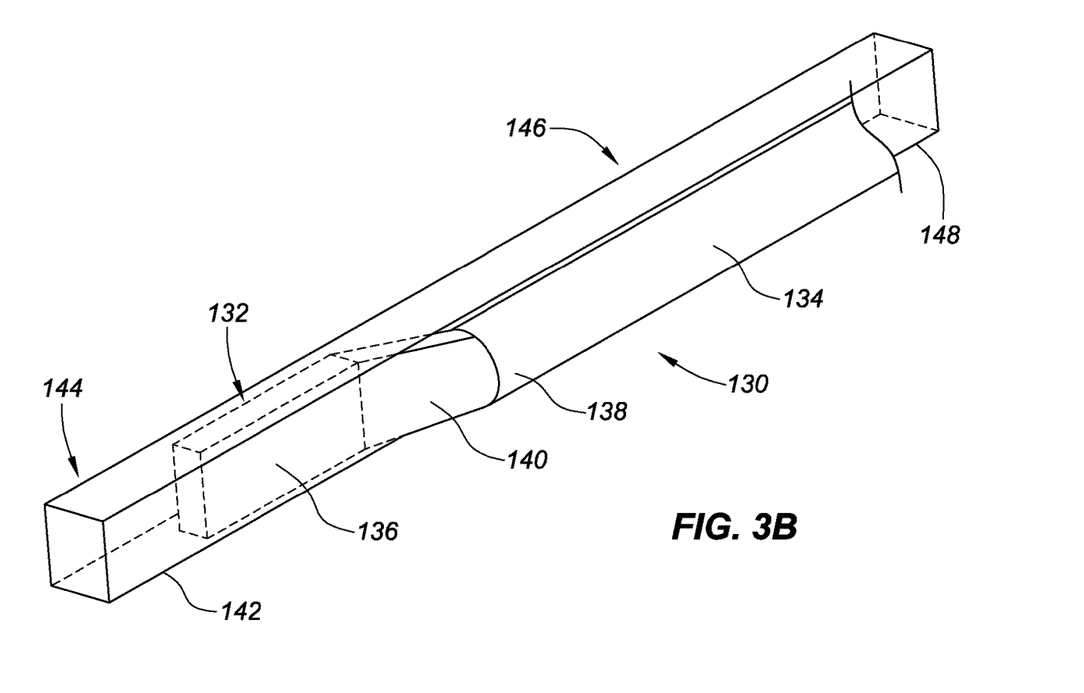
FIG. 3B illustrates the pullwire depicted in FIG. 3A with the first type of anchor feature embedded in an anchor segment of a deflectable catheter shaft, in accordance with embodiments of the present disclosure.

FIG. 3B illustrates the pullwire 130 with the first type of anchor feature depicted in FIG. 3A embedded in an anchor segment of a deflectable catheter shaft, in accordance with embodiments of the present disclosure. As further depicted in FIG. 3B, the pullwire shaft 134 can be disposed along a surface of a tubular elongated body 146, as previously discussed herein. As depicted, the pullwire shaft 134 can be partially disposed beneath an inner body surface 148 of the tubular elongated body 146. For example, a channel can be formed in the inner body surface 148 in which the pullwire shaft 134 can be disposed. In some embodiments, the pullwire shaft 134 can be disposed entirely within the wall of the tubular elongated body 146 or can be disposed entirely within a lumen defined by the inner body surface 148. Although not depicted, the pullwire shaft 134 can be disposed in a pullwire liner, as previously discussed herein.

As previously mentioned, the flattened end 136 of the anchor feature 132 can be connected to the pullwire distal end 138 via the offset transition 140. In an example, the offset transition 140 can cause the flattened end 136 to be offset with respect to a longitudinal axis of the pullwire shaft 134. This can allow for the flattened end 136 to be completely embedded in a wall of the anchor segment 144. For example, the flattened end 136 can be completely embedded beneath an inner surface 142 of the anchor segment 144 and/or inner body surface 148 of the tubular elongated body 146. This can be beneficial when the pullwires and/or their respective pullwire liners are not completely embedded in a wall of a tubular elongated body 146 of a deflectable electrophysiology catheter, as similarly depicted in FIG. 2. For example, when the pullwire 130 is disposed within a central lumen of the tubular elongated body 146 or is partially disposed in an inner wall of the tubular elongated body 146 (e.g., located both in the central lumen 106 and in the wall of the tubular elongated body 104 as depicted in FIG. 2), the offset transition 140 can position the flattened end 136 such that it is completely embedded beneath the inner surface 142 of the anchor segment 144, as depicted in FIG. 3B.

Figures 4A, 4B:
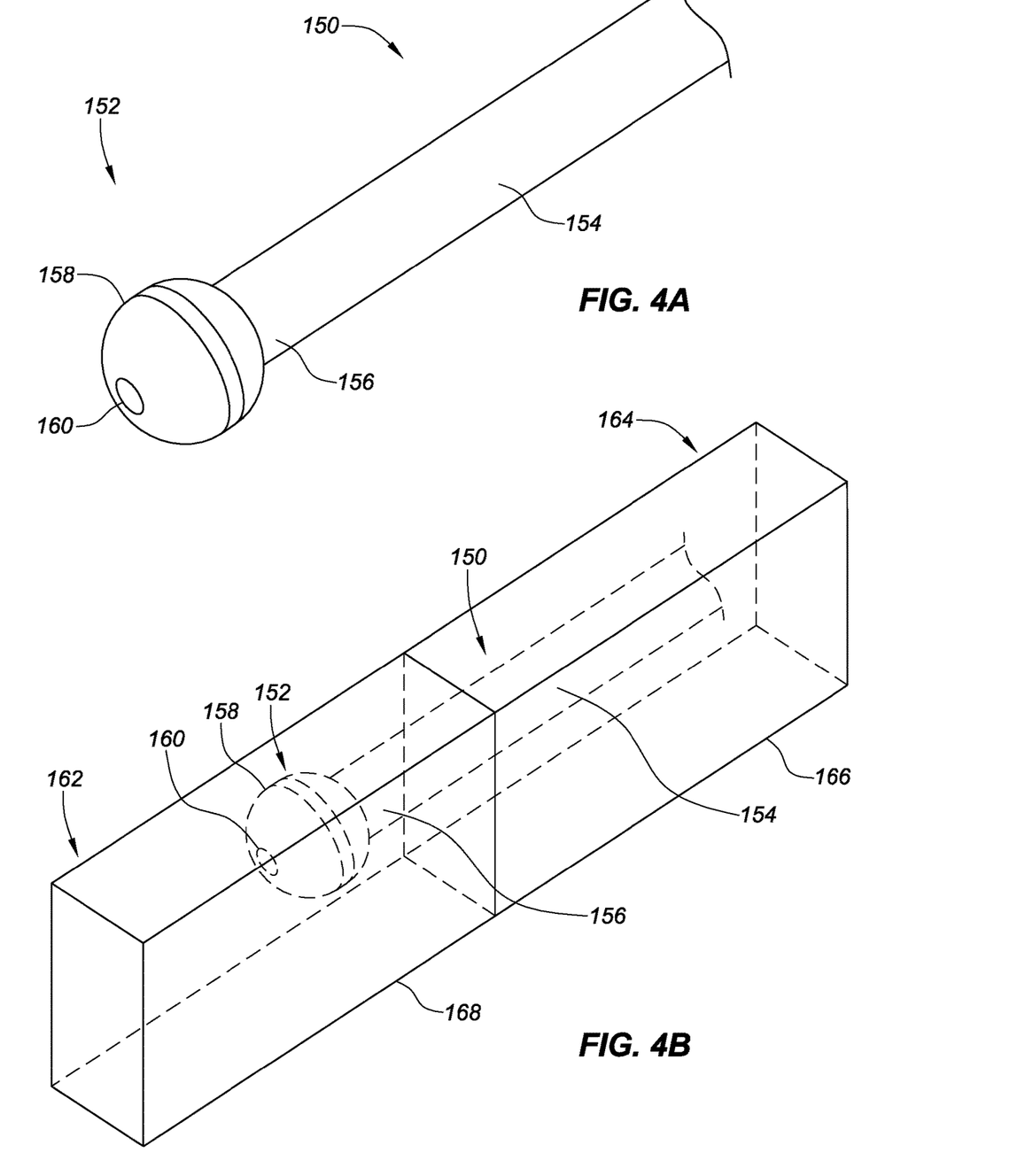
FIG. 4A illustrates a pullwire with a second type of anchor feature, in accordance with embodiments of the present disclosure.
FIG. 4B illustrates the pullwire depicted in FIG. 4A with the second type of anchor feature embedded in an anchor segment of a deflectable catheter shaft, in accordance with embodiments of the present disclosure.

FIG. 4A illustrates a pullwire 150 with a second type of anchor feature 152, in accordance with embodiments of the present disclosure. The pullwire 150 can include a pullwire shaft 154, which can be an elongated cylindrical structure in some embodiments. The pullwire shaft 154 can be formed from a metal, such as nitinol, or other suitable non-metallic materials. In some embodiments, the anchor feature 152 can include a rounded end 158, which is attached to a pullwire distal end 156 and can have a diameter that is larger than that of the pullwire. For example, as depicted in FIG. 4B, the anchor feature 152 can be spherical in shape. Although the rounded end 158 is depicted as spherical in shape, the end can be other shapes, including a cube, cylinder, etc. The rounded end 158 can be a welded ball end in some embodiments, formed through placement of a bead of weld on the pullwire distal end 156. In some embodiments, as depicted, the rounded end 158 can have a hole 160 formed in a center of the rounded end through which the pullwire distal end 156, or a portion thereof, can be inserted. In some embodiments, a bead of weld can be used to attach the rounded end 158 onto the pullwire distal end 156 and/or the rounded end 158 can be press fit and/or crimped onto the pullwire distal end 156.

FIG. 4B illustrates the pullwire shaft 154 with the second type of anchor feature 152 depicted in FIG. 4A embedded in an anchor segment 162 of a deflectable catheter shaft, in accordance with embodiments of the present disclosure. Although the pullwire shaft 154 can be disposed in a lumen of a pullwire liner, the pullwire liner has not been depicted for ease of illustration. As depicted in FIG. 4B, the rounded end 158 is disposed on the pullwire distal end 156, which is straight, and is embedded in the sidewall of an anchor segment. Because the entire pullwire shaft 154 is embedded in a sidewall of an elongated body portion 164 of the deflectable catheter shaft, an offset transition may not be needed to position the anchor feature 152 in the sidewall of the anchor segment 162. For example, the anchor feature 152 can be disposed in the anchor segment 162 such that it is completely embedded within the anchor segment 162.

However, although not depicted, the pullwire shaft 154 can be disposed in a central lumen defined by the elongated body 164 or can be partially disposed in the central lumen and within a channel formed in an inner surface 166 of the elongated body 164 and/or inner surface 168 of the anchor segment. In such an embodiment, the rounded end 158 can be attached to the pullwire distal end 156 via an offset transition, as further discussed in relation to FIG. 4A.

Figures 5A, 5B:
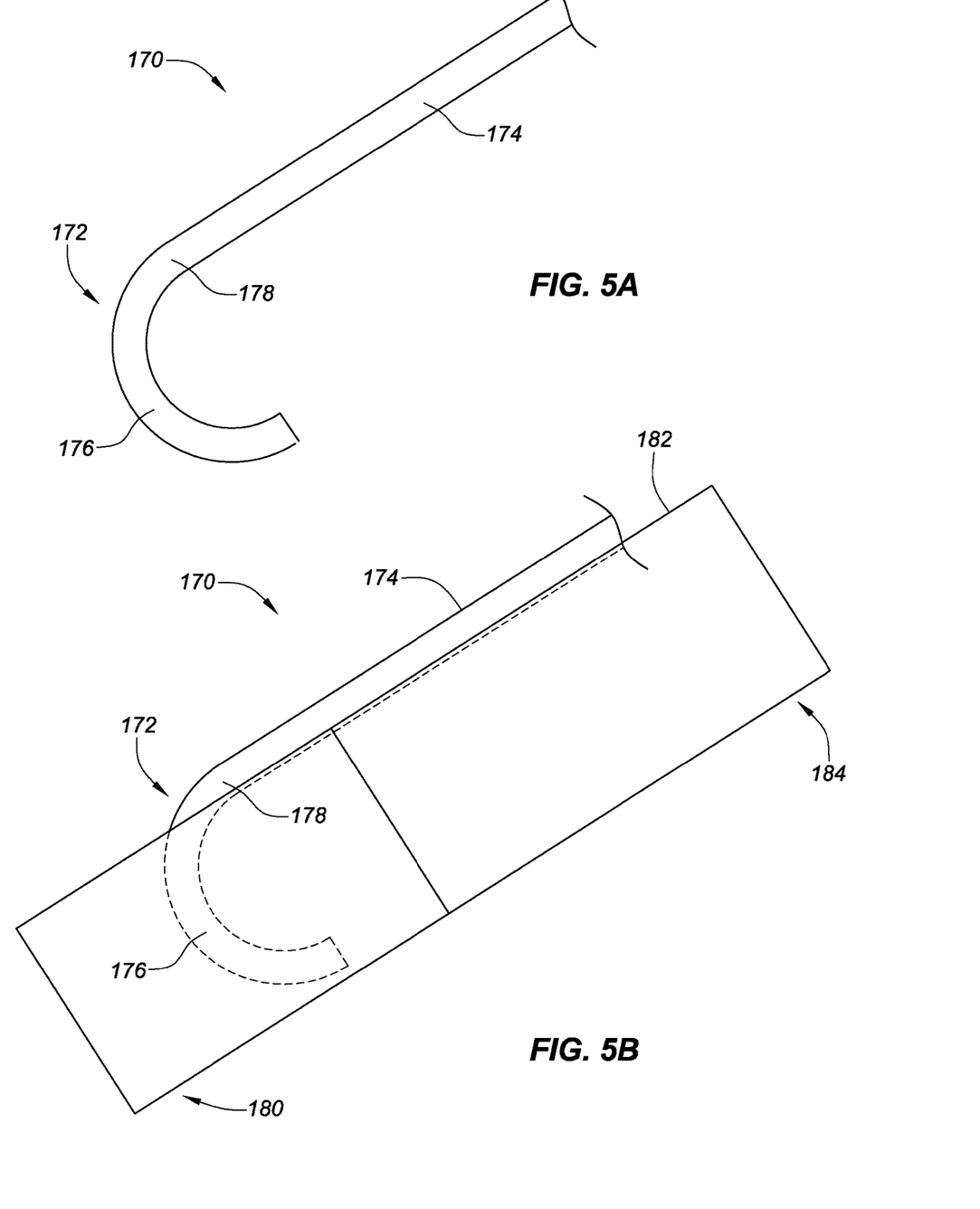
FIG. 5A illustrates a pullwire with a third type of anchor feature, in accordance with embodiments of the present disclosure.
FIG. 5B illustrates the pullwire depicted in FIG. 5A with the third type of anchor feature embedded in an anchor segment of a deflectable catheter shaft, in accordance with embodiments of the present disclosure.

FIG. 5A illustrates a pullwire 170 with a third type of anchor feature 172, in accordance with embodiments of the present disclosure. The pullwire 170 can include a pullwire shaft 174, which can be an elongated cylindrical structure in some embodiments. The pullwire shaft 174 can be formed from a metal, such as nitinol, or other suitable non-metallic materials. In some embodiments, the anchor feature 172 can comprise a hooked distal end 176 that includes a bend in a pullwire distal end 178. Although the hooked distal end 176 is depicted as being a curved hook distal end, the hooked distal end can be comprised of straightened components. The hooked distal end 176 can be attached to the pullwire distal end 178, in some embodiments. The hooked distal end 176 can be disposed within a sidewall of an anchor segment, as previously discussed herein.

FIG. 5B illustrates the pullwire 170 depicted in FIG. 5A with the third type of anchor feature 172 embedded in an anchor segment 180 of a deflectable catheter shaft, in accordance with embodiments of the present disclosure. In some embodiments, the pullwire shaft 174 can be partially disposed in a central lumen defined by an interior surface 182 of an elongated body 184 and the hooked distal end 176 can be embedded in the anchor segment 180. Although not depicted, the pullwire shaft 174 can be disposed in a pullwire liner, which can be attached to the interior surface 182 of the elongated body 184. Accordingly, the hooked distal end 176 can be disposed within the anchor segment 180, providing for an attachment between the anchor segment 180 and the pullwire shaft 174. In some embodiments, the anchor segment 180 can be reflowed around the hooked distal end 176.

FIG. 6 illustrates a deflectable catheter shaft 190 in a partially assembled state, in accordance with embodiments of the present disclosure. In some embodiments, the deflectable catheter shaft 190 can include an elongated body 192 that is formed from a polymer material. The tubular elongated body 192 can include a wall 204, the interior of which defines a central lumen that extends therethrough. In FIG. 6, the central lumen is depicted as having a mandrel 194 disposed therein, which can be used for assembly of the deflectable catheter shaft 190.

In some embodiments, the elongated body 192 can be deflected by one or more pullwires (e.g., pullwire 196) that extend through the wall of the tubular elongated body 192 and/or through the central lumen of the elongated body 192. The pullwire 196 can include a pullwire proximal end and a pullwire distal end and can be disposed within pullwire liners (e.g., pullwire liner 198). In an example, the pullwire 196 can be disposed entirely within the wall 204 of the tubular elongated body 192, in the central lumen of the elongated body 192, or partially within the central lumen of the elongated body 192 and in the wall 204 of the tubular elongated body 192. To aid in assembly, the pullwire 196 can be inserted into channels 200-1, 200-2 defined in an exterior surface of the mandrel 194. The elongated body 192 can then be disposed over the mandrel 194 that holds the pullwire liner 198 and the pullwire 196. As depicted in FIG. 6, the elongated body 192 has been only partially inserted over the mandrel 194 and associated components. For example, the mandrel 194 and associated components can be further inserted through the central lumen defined by the elongated body 192 toward a distal end 210 of the elongated body 192.

For ease of illustration, only one pullwire 196 and associated pullwire liner 198 is depicted in FIG. 6, however, another pullwire and associated pullwire liner can be disposed within the channel 200-2. As previously discussed, two pullwires can provide for a bidirectional deflectable catheter, however, fewer than or greater than two pullwires 196 can be included in the elongated body 192. For example, one pullwire can be included in the elongated body 192, resulting in a unidirectional deflectable catheter; or more than two pullwires can be included in the elongated body 192, resulting in an omnidirectional deflectable catheter.

As depicted in FIG. 6, the first pullwire 196 can include an anchor feature 202 that is coupled to a distal end of the pullwire 196 via an offset transition 205, as previously discussed. Upon assembly of the deflectable catheter shaft 190, the anchor feature 202 can be embedded in a sidewall 206 of an anchor segment 208. As depicted in FIG. 6, the anchor segment 208 is separate from the elongated body 192 and has not been connected to the distal end 210 of the elongated body 192. In some embodiments, the elongated body 192 can be inserted onto the mandrel 194, such that a distal end of the mandrel 194 and the pullwire assembly protrude from the distal end 210 of the elongated body 192. The anchor segment 208 can then be inserted onto the distal end of the mandrel 194, such that a proximal end 212 of the anchor segment 208 is in contact with the distal end 210 of the elongated body 192. In some embodiments, the anchor feature 202 can be disposed adjacent to an interior wall of the anchor segment 208 and can be formed from a polymer material.

Upon positioning of the mandrel 194 and associated components within the elongated body 192 and within the anchor segment 208, the mandrel 194, associated components, elongated body 192, and the anchor segment 208 can be heated to a particular temperature, causing the anchor segment 208 (e.g., polymer anchor segment) and the elongated body 192 to reflow. For example, upon reflow of the anchor segment 208 and elongated body 192, the anchor segment 208 can melt around the anchor features 202, causing the anchor features to be disposed within the sidewall 206 of the anchor segment 208.

As depicted in FIG. 6, a braid layer 214 can be disposed about an inner surface of the elongated body 192, between the inner surface of the elongated body 192 and the pullwire liner 198, pullwire 196, and anchor features 202. Although not depicted, the braid layer 214 can extend into a lumen formed by the anchor segment 208, such that it is disposed adjacent an interior surface of the anchor segment 208. In some embodiments, upon full insertion of the elongated body 192 and the anchor segment 208 onto the mandrel 194, such that the mandrel 194 extends through central lumens defined by the anchor segment 208 and the elongated body 192, a proximal end 212 of the anchor segment 208 can be coupled with the distal end 210 of the elongated body 192 via the reflow process. For example, as the mandrel 194 and the components disposed on the mandrel 194 are heated, the anchor segment 208 and the elongated body 192 can be reflowed and can be joined together. Upon reflow of the anchor segment 208 and the elongated body 192, the mandrel 194 can be removed to form a deflectable electrophysiology catheter, as depicted in FIG. 2. In some embodiments, the reflow can occur at a temperature of approximately 300 to 600 degrees Fahrenheit, although the reflow can occur at temperature outside of that range in some embodiments.

In some embodiments, the anchor features 202 can extend from an inner surface of the braid layer 214 through the braid layer 214 and into the sidewall 206 of the anchor segment. For example, the braid layer can cover an inner surface of the elongated body 192 and an inner surface of the anchor segment 208. Accordingly, for the anchor features 202 to be embedded in the sidewall 206 of the anchor segment 208, the anchor features 202 can pass through a weave of the braid layer 214 and/or a hole formed in the braid layer.

In some embodiments, the anchor features 202 can first be embedded in the sidewall 206 of the anchor segment. The anchor features 202, along with the pullwire assemblies that include the pullwire 196 and the pullwire liner 198 can then be placed onto the mandrel.

In some embodiments, a low friction liner can be disposed around an interior surface of the elongated body 192 and/or the anchor segment 208. The low friction liner can extend from a proximal end of the elongated body 192 to a distal end of the anchor segment 208. For instance, the low friction liner can be a tubular liner that is disposed about the mandrel 194 on which the components of the deflectable catheter shaft 190 are placed. Accordingly, the low friction liner can cover the inside wall of the elongated body 192 as well as the portions of the pullwire liner 198 that are exposed in the central lumen of the elongated body. In some embodiments, the low friction liner can extend into the anchor segment and cover the inside wall of the anchor segment. In some embodiments, the low friction liner can be formed from a polytetrafluoroethylene material (e.g., Teflon™), or another type of low friction material.

Figure 7:
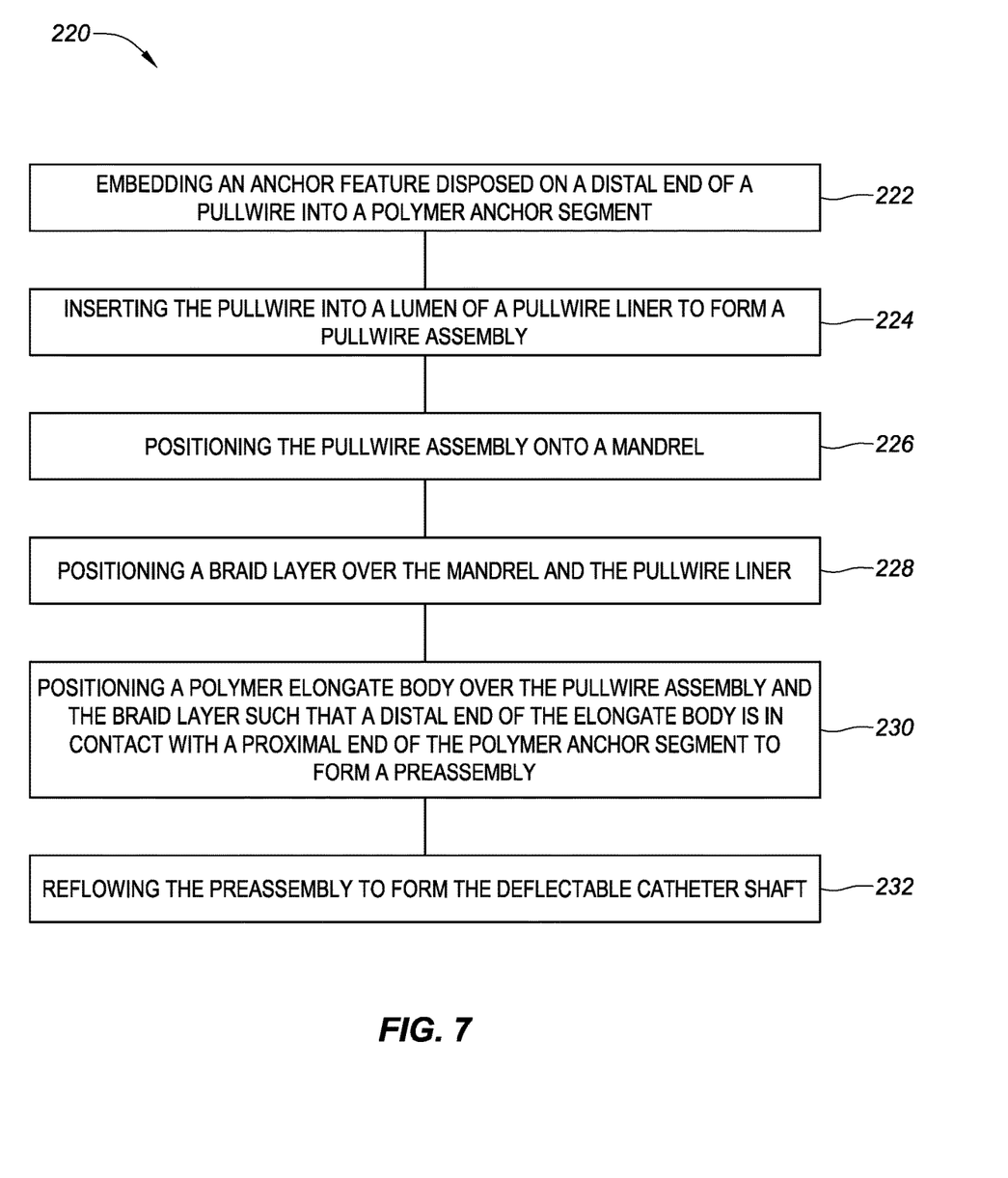
FIG. 7 illustrates a method flow diagram for the assembly of a deflectable catheter shaft, in accordance with embodiments of the present disclosure.

FIG. 7 illustrates a method flow diagram 220 for the assembly of a deflectable catheter shaft, in accordance with embodiments of the present disclosure. In some embodiments, the method 220 can include embedding 222 an anchor feature disposed on a distal end of a pullwire into a polymer anchor segment. Although only one pullwire is discussed herein, embodiments of the present disclosure can include more than one pullwire. In some embodiments, the anchor feature can be an anchor feature such as those discussed herein, for example, in relation to FIGS. 2 to 6. The polymer anchor segment can be a tubular segment that defines a lumen that extends therethrough. The anchor feature can be embedded in a sidewall of the tubular segment. In an example, the polymer tubular segment can be melt processed and during the melt processing of the polymer tubular segment, the anchor feature can be embedded in the sidewall of the tubular segment. As previously discussed herein, in some embodiments, the anchor segment can be formed from an inner tubular segment and an outer tubular segment, both of which are formed from a polymer. The anchor feature can be disposed between the inner tubular segment and the outer tubular segment and the inner tubular segment and the outer tubular segment can be reflowed, thus causing the anchor feature to be embedded between the inner tubular segment and the outer tubular segment.

In some embodiments, the method 220 can include inserting 224 the pullwire into a lumen of a pullwire liner to form a pullwire assembly. The pullwire liner can be a polymer tube that houses the pullwire and provides a lubricious passageway through which the pullwire can pass. In some embodiments, the method 220 can include positioning 226 the pullwire assembly on a mandrel. The mandrel can include channels 200-1, 200-2, as depicted in FIG. 6, into which the pullwire liners and the respective pullwires can be disposed. The mandrel can allow for uniform assembly of the deflectable catheter shaft by providing defined areas into which particular components of the deflectable catheter shaft can be positioned.

In some embodiments, the method 220 can include positioning 228 a braid layer over the mandrel and the pullwire liner. In an example, the braid layer can be formed from a metal and/or fiber braid. The metal and/or fiber braid layer can be formed as a tubular braid layer through which the mandrel and pullwire liner can be inserted. In some embodiments, a liner made from a Teflon™ material can first be positioned onto the mandrel, before the pullwire assembly is positioned onto the mandrel. The liner can line an interior wall of the deflectable catheter shaft, providing a smooth and low friction surface through which other components and/or devices can be inserted.

In some embodiments, the method 220 can include positioning 230 a polymer elongated body over the pullwire assembly and the braid layer such that a distal end of the elongated body is in contact with a proximal end of the polymer anchor segment, thus forming a preassembly. The elongated body can be tubular and can define a central lumen through which the mandrel and the pullwire assembly can be inserted. The anchor segment can also be positioned onto the mandrel, such that the proximal end of the anchor segment touches, or is in close relation to, the distal end of the elongated body.

In some embodiments, the method 220 can include reflowing 232 the preassembly to form the deflectable catheter shaft. In an example, the preassembly can be heated such that the proximal end of the anchor segment fuses with the distal end of the elongated body. Additionally, the braid layer can be fused with an inner wall of the elongated body and the pullwire liner and the liner can be fused to the braid layer and the pullwire liner. In some embodiments, the reflow can occur at a temperature of approximately 300 to 600 degrees Fahrenheit, although the reflow can occur at temperature outside of that range in some embodiments.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a deflectable catheter shaft with pullwire anchor feature has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A deflectable catheter shaft comprising:
  a tubular elongated body comprising a tubular wall, wherein an inner surface of the tubular wall circumferentially surrounds and defines a central lumen extending a length of the tubular elongated body, and wherein the tubular wall extends along a longitudinal axis of the tubular elongated body and comprises a tubular wall distal end, a tubular wall proximal end, and a tubular wall anchor segment attached to the tubular wall distal end at an interface wall and extending distally from the tubular wall distal end; and
  a pullwire comprising a pullwire proximal end, an oblique offset transition portion, an anchor portion having a modified shape having a cross-sectional shape different from a cross-sectional shape of the pullwire proximal end and extending directly from the offset transition portion, and a pullwire shaft portion that extends between and connects the pullwire proximal end and the offset transition portion, wherein the pullwire shaft portion extends along the inner surface of the tubular wall within the central lumen, wherein the offset transition portion offsets the anchor portion laterally from a longitudinal axis of the pullwire shaft portion, and wherein the modified shape of the anchor portion and an embedded portion of the offset transition portion form an embedded portion of the pullwire that is embedded within the tubular wall anchor segment via molding of the tubular wall anchor segment so that:
    the embedded portion of the pullwire is in direct contact with only the tubular wall anchor segment and a non-embedded portion of the offset transition portion;

the non-embedded portion of the offset transition portion extends into the central lumen from the embedded portion of the offset transition portion, and all force applied to the embedded portion of the pullwire by the non-embedded portion of the offset transition portion is transferred directly to the tubular wall anchor segment by the embedded portion of the pullwire.

2. The deflectable catheter shaft of claim 1, wherein the tubular wall anchor segment is formed from a moldable material that has a durometer greater than that of adjacent portions of the tubular wall that abut the tubular wall anchor segment.

3. The deflectable catheter shaft of claim 1, further comprising a pullwire liner that defines a pullwire lumen through which the pullwire extends, wherein the pullwire liner and the pullwire form a pullwire assembly.

4. The deflectable catheter shaft of claim 3, wherein the pullwire liner is attached to the inner surface of the tubular wall.

5. The deflectable catheter shaft of claim 4, wherein a low-friction material is adhered to the pullwire liner and the inner surface of the tubular wall.

6. The deflectable catheter shaft of claim 3, further comprising a braid layer disposed between the inner surface of the tubular wall and the pullwire liner.

7. The deflectable catheter shaft of claim 1, wherein the anchor portion comprises a flattened portion of the pullwire.

8. The deflectable catheter shaft of claim 1, wherein the pullwire is formed from a non-metallic material.

9. A deflectable catheter shaft comprising:
a tubular elongated body comprising a tubular wall, wherein an inner surface of the tubular wall circumferentially surrounds and defines a central lumen, and wherein the tubular wall extends along a longitudinal axis of the tubular elongated body and comprises a tubular wall distal end, a tubular wall proximal end, and a tubular wall anchor segment attached to the tubular wall distal end at an interface wall and extending distally from the tubular wall distal end;
a first pullwire comprising a first pullwire proximal end, a first pullwire distal end portion, a first oblique offset transition portion, a first anchor portion having a modified shape with a cross-sectional shape different from a cross-sectional shape of the first pullwire proximal end and extending directly from the first offset transition portion, and a first pullwire shaft portion that extends between and connects the first pullwire proximal end and the first offset transition portion, wherein the first pullwire shaft portion extends along the inner surface of the tubular wall within the central lumen, wherein the first offset transition portion offsets the first anchor portion laterally from a first longitudinal axis of the first pullwire shaft portion, and wherein the modified shape of the first anchor portion and an embedded portion of the first offset transition portion form an embedded portion of the first pullwire that is embedded within the tubular wall anchor segment via molding of the tubular wall anchor segment so that:

the embedded portion of the first pullwire is in direct contact with only the tubular wall anchor segment and a non-embedded portion of the first offset transition portion;

the non-embedded portion of the first offset transition portion extends into the central lumen from the embedded portion of the first offset transition portion, and all force applied to the embedded portion of the first pullwire by the non-embedded portion of the first offset transition portion is transferred directly to the tubular wall anchor segment by the embedded portion of the first pullwire; and a second pullwire comprising a second pullwire proximal end, a second pullwire distal end portion, a second oblique offset transition portion, a second anchor portion having a modified shape with a cross-sectional shape different from a cross-sectional shape of the second pullwire proximal end and extending directly from the second offset transition portion, and a second pullwire shaft portion that extends between and connects the second pullwire proximal end and the second offset transition portion, wherein the second pullwire shaft portion extends along the inner surface of the tubular wall within the central lumen, wherein the second offset transition portion offsets the second anchor portion laterally from a longitudinal axis of the second pullwire shaft portion, and wherein the modified shape of the second anchor portion and an embedded portion of the second offset transition portion form an embedded portion of the second pullwire that is embedded within the tubular wall anchor segment so that:

the embedded portion of the second pullwire is in direct contact with only the tubular wall anchor segment and a non-embedded portion of the second offset transition portion, the non-embedded portion of the second offset transition portion extends into the central lumen from the embedded portion of the second offset transition portion, and all force applied to the embedded portion of the second pullwire by the non-embedded portion of the second offset transition portion is transferred directly to the tubular wall anchor segment by the embedded portion of the second pullwire.

10. The deflectable catheter shaft of claim 9, wherein the tubular wall anchor segment is coaxial with the longitudinal axis of the tubular elongated body.

11. The deflectable catheter shaft of claim 9, wherein the tubular wall anchor segment is formed from a moldable material that has a durometer greater than that of adjacent portions of the tubular wall that abut the tubular wall anchor segment.

12. The deflectable catheter shaft of claim 9, wherein the first pullwire and the second pullwire are disposed between the tubular wall and a liner made from a polytetrafluoroethylene material.

13. The deflectable catheter shaft of claim 9, wherein the tubular wall anchor segment and the tubular elongated body are formed from at least one polymer material.

* * * * *